(12) United States Patent
Arai et al.

(10) Patent No.: US 10,487,066 B2
(45) Date of Patent: Nov. 26, 2019

(54) METHOD OF PRODUCING SUGAR ALCOHOL

(71) Applicant: Toray Industries, Inc., Tokyo (JP)

(72) Inventors: Takahiro Arai, Kamakura (JP); Masateru Ito, Kamakura (JP); Hiroyuki Kurihara, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/999,598

(22) PCT Filed: Feb. 16, 2017

(86) PCT No.: PCT/JP2017/005611
§ 371 (c)(1),
(2) Date: Aug. 17, 2018

(87) PCT Pub. No.: WO2017/142000
PCT Pub. Date: Aug. 24, 2017

(65) Prior Publication Data
US 2019/0177290 A1 Jun. 13, 2019

(30) Foreign Application Priority Data

Feb. 17, 2016 (JP) .................. 2016-027694
Sep. 6, 2016 (JP) .................. 2016-173698

(51) Int. Cl.
| C07D 307/20 | (2006.01) |
| C07C 29/141 | (2006.01) |
| C07C 31/18 | (2006.01) |
| C07C 31/26 | (2006.01) |
| C12P 19/14 | (2006.01) |
| C13K 13/00 | (2006.01) |
| B01D 61/14 | (2006.01) |
| B01D 69/02 | (2006.01) |
| C07B 61/00 | (2006.01) |

(52) U.S. Cl.
CPC ......... *C07D 307/20* (2013.01); *B01D 61/145* (2013.01); *B01D 69/02* (2013.01); *C07C 29/141* (2013.01); *C07C 31/18* (2013.01); *C07C 31/26* (2013.01); *C12P 19/14* (2013.01); *C13K 13/00* (2013.01); *B01D 2325/20* (2013.01); *C07B 61/00* (2013.01)

(58) Field of Classification Search
CPC .... B01D 61/145; B01D 69/02; C07C 29/141; C12P 19/14
USPC ........................................ 549/476
See application file for complete search history.

(56) References Cited

U.S. PATENT DOCUMENTS

| 5,562,777 | A | 10/1996 | Farone et al. |
| 5,580,389 | A | 12/1996 | Farone et al. |
| 5,597,714 | A | 1/1997 | Farone et al. |
| 5,620,877 | A | 4/1997 | Farone et al. |
| 5,726,046 | A | 3/1998 | Farone et al. |
| 5,782,982 | A | 7/1998 | Farone et al. |
| 5,820,687 | A | 10/1998 | Farone et al. |
| 2005/0211239 | A1 | 9/2005 | Koivikko et al. |
| 2007/0113840 | A1 | 5/2007 | Koivikko et al. |
| 2008/0060638 | A1 | 3/2008 | Koivikko et al. |
| 2011/0008826 | A1 | 1/2011 | Hanakawa et al. |
| 2011/0250637 | A1 | 10/2011 | Kurihara et al. |
| 2013/0273608 | A1 | 10/2013 | Hanakawa et al. |
| 2014/0178937 | A1 | 6/2014 | Minamino et al. |
| 2014/0287461 | A1 | 9/2014 | Kurihara et al. |
| 2015/0354018 | A1 | 12/2015 | Nishino et al. |
| 2017/0275663 | A1 | 9/2017 | Minamino et al. |

FOREIGN PATENT DOCUMENTS

| CN | 104402676 | * | 3/2015 | |
| JP | 11-506934 | A | 6/1999 | |
| JP | 2001-079411 | A | 3/2001 | |
| JP | 2001-095594 | A | 4/2001 | |
| JP | 2005-533494 | A | 11/2005 | |
| JP | 2008-056599 | A | 3/2008 | |
| JP | 2008-161125 | A | 7/2008 | |
| JP | 2008-535664 | A | 9/2008 | |
| JP | 2014-128213 | A | 7/2014 | |
| JP | 2014-196294 | A | 10/2014 | |
| JP | 2016-007160 | A | 1/2016 | |
| JP | 2016-079169 | A | 5/2016 | |
| WO | 2009/110374 | A1 | 9/2009 | |
| WO | 2010/067785 | A1 | 6/2010 | |
| WO | 2013/018694 | A1 | 2/2013 | |
| WO | 2014/065364 | A1 | 5/2014 | |
| WO | WO-2016028851 | A1 * | 2/2016 | ........... C07D 307/20 |
| WO | 2016/035875 | A1 | 3/2016 | |

OTHER PUBLICATIONS

Morris D. Argyle et al., "Heterogeneous Catalyst Deactivation and Regeneration: A Review," *Catalysis* 2015, 5, 145-269.

* cited by examiner

*Primary Examiner* — Daniel R Carcanague
(74) *Attorney, Agent, or Firm* — DLA Piper LLP (US)

(57) ABSTRACT

In the present invention, a sugar alcohol can be efficiently produced from a cellulose-containing biomass by carrying out a step (1) of filtering an aqueous sugar solution, which is obtained by hydrolysis of a cellulose-containing biomass, by passing the solution through a separation membrane having a molecular cut-off of 300-800 so as to remove catalyst poisons to the non-permeate side and collecting a sugar solution from the permeate side, and a step (2) of subjecting the sugar solution obtained in step (1) to a hydrogenation reaction in the presence of a metal catalyst.

7 Claims, No Drawings

METHOD OF PRODUCING SUGAR ALCOHOL

TECHNICAL FIELD

This disclosure relates to a method of producing sugar alcohol from a cellulose-containing biomass.

BACKGROUND

Synthesis process of chemicals using sugar as a raw material is utilized in the production of various industrial raw materials, and particularly synthesis process of sugar alcohol by a hydrogenation reaction of sugar is the representative example. At present, materials derived from edible raw materials such as sugarcane, starch and sugar beets are industrially used as sugar for the synthesis raw materials. However, because of increases in edible raw material prices due to future increase in the world's population or ethical aspects of competition with edibles, construction of a process of efficiently producing a sugar solution from renewable non-edible resources, that is, a cellulose-containing biomass, or a process of efficiently converting the sugar solution obtained as a synthesis raw material into an industrial raw material is becoming a future problem.

As the conventional technology of obtaining sugar from a cellulose-containing biomass, a method of hydrolyzing cellulose and hemicellulose in a biomass into monosaccharide represented by glucose and xylose using concentrated sulfuric acid (JP-T-11-506934) and a method of performing pretreatment improving hydrolysis reactivity of a cellulose-containing biomass, and then hydrolyzing the biomass by an enzyme reaction are generally known (JP-A-2001-95594). Also, a method of obtaining a sugar solution by purifying a sugar aqueous solution after hydrolysis using an ultrafiltration membrane, a nanofiltration membrane, a reverse osmosis membrane or the like is reported (WO 2013/018694, WO 2009/110374 and WO 2010/067785).

As the technology relating to a method of producing sugar alcohol from sugar derived from a cellulose-containing biomass by a hydrogenation reaction, a method of producing a xylose polymer reduced substance that is sugar alcohol by removing low molecular weight contaminants contained in a xylose polymer-containing aqueous solution obtained by treating a xylan-containing biomass with specific high pressure hot water, from the permeation side of a nanofiltration membrane, and then hydrogenating a xylose polymer collected from the non-permeation side at high temperature under high pressure in the presence of a metal catalyst is known (JP-A-2008-56599).

In a hydrogenation reaction using a metal catalyst, when a substance poisoning a catalyst (catalyst poison) is present, the reaction does not proceed. Therefore, it is required to remove the catalyst poison as possible. Low molecular weight organic substances such as a nitrogen compound, a sulfur compound and a phosphorus compound and metals such as Ag, Hg, Pb, Bi, Sn, Cd and As are known as specific examples of the catalyst poison for a metal catalyst (Catalyst 2015, 5, 145-269). For removal of those catalyst poisons, a method of adsorbing and removing those by performing an activated carbon treatment or an ion-exchanged resin treatment are general (JP-A-2001-79411).

We found that when sugar alcohol is produced from a sugar aqueous solution as a raw material obtained by hydrolysis of a cellulose-containing biomass, a hydrogenation reaction of a sugar alcohol is inhibited by that catalyst poisons contained in the sugar aqueous solution. There is thus a need to provide a method of efficiently producing sugar alcohol from a cellulose-containing biomass by a simple method of removing catalyst poisons derived from the cellulose-containing biomass.

SUMMARY

We found that catalyst poisons contained in a sugar aqueous solution obtained by hydrolysis of a cellulose-containing biomass are not low molecular weight organic substances and metals generally known, but are relatively high molecular weight substances, and the catalyst poisons can be simply removed by a separation membrane.

We thus provide the following [1] to [9]:

[1] A method of producing a sugar alcohol from a cellulose-containing biomass as a raw material, including:

step (1): a step of filtering a sugar aqueous solution obtained by hydrolysis of the cellulose-containing biomass, through a separation membrane having a molecular weight cut-off of 300 to 800 to remove a catalyst poison to a non-permeation side and collecting a sugar solution from a permeation side; and step (2): a step of subjecting the sugar solution obtained in the step (1) to a hydrogenation reaction in a presence of a metal catalyst.

[2] The method of producing a sugar alcohol according to [1] above, in which the separation membrane in the step (1) is a separation membrane having a molecular weight cut-off of 300 to 500.

[3] The method of producing a sugar alcohol according to [1] above, in which the separation membrane in the step (1) is a separation membrane having a molecular weight cut-off of 600 to 800.

[4] The method of producing a sugar alcohol according to any one of [1] to [3] above, in which the metal catalyst in the step (2) is a ruthenium catalyst or a Raney nickel catalyst.

[5] The method of producing a sugar alcohol according to any one of [1] to [4] above, in which the sugar alcohol comprises sorbitol and/or xylitol as a main component.

[6] A method of producing an anhydrous sugar alcohol, including a step of producing a sugar alcohol by the production method according to any one of [1] to [5] above, and a step of subjecting the sugar alcohol to a dehydration reaction.

[7] The method of producing an anhydrous sugar alcohol according to [6] above, in which the anhydrous sugar alcohol comprises a sorbitan and/or a xylitan as a main component.

[8] A method of producing an anhydrous sugar alcohol ester, including a step of producing a sugar alcohol by the production method according to any one of [1] to [5] above, a step of producing an anhydrous sugar alcohol by the production method according to [6] above, and a step of subjecting the anhydrous sugar alcohol to a condensation reaction with a saturated or unsaturated fatty acid.

[9] The method of producing an anhydrous sugar alcohol ester according to [8] above, in which the anhydrous sugar alcohol ester comprises a sorbitan ester and/or a xylitan ester as a main component.

Sugar alcohol can be produced in high yield from a cellulose-containing biomass.

DETAILED DESCRIPTION

A cellulose-containing biomass means a resource derived from an organism containing 5 wt % or more of a cellulose. Examples of the cellulose-containing biomass specifically include herbaceous biomass such as bagasse, switchgrass, napier grass, erianthus, corn stover, rice straw and wheat straw, and woody biomass such as trees and waste of building materials. Those cellulose-containing biomass contain lignin that is aromatic polymer and cellulose/hemicellulose and are therefore called lignocellulose. A sugar solution containing monosaccharide usable as a synthetic raw material for producing chemicals, specifically, a sugar solution comprising xylose and glucose as main components, can be obtained by hydrolyzing cellulose and hemicellulose that are polysaccharide components contained in a cellulose-containing biomass.

Examples of the hydrolysis treatment of the cellulose-containing biomass specifically include, as a chemical treatment method, an acid treatment treating with diluted sulfuric acid, a sulfite or the like at high temperature under high pressure; an alkali treatment treating with an alkaline aqueous solution such as calcium hydroxide or sodium hydroxide; an ammonia treatment treating with liquid ammonia, an ammonia gas or an ammonia aqueous solution; and a hydrothermal treatment treating with pressurized hot water. In addition to those hydrolysis treatments, a hydrolysis treatment with a saccharifying enzyme may be performed.

The acid treatment generally has the characteristic that lignin is dissolved to induce hydrolysis of easily soluble hemicellulose component, and then hardly soluble cellulose component is decomposed and therefore a liquid containing a large amount of xylose derived from hemicellulose can be obtained. Although the number of treatment is not particularly limited, by setting the acid treatment step to two or more stages, hydrolysis conditions suitable for hemicellulose and cellulose can be selectively set, and decomposition efficiency and sugar yield can be improved. The acid used in the acid treatment is not particularly limited so long as it causes hydrolysis, but sulfuric acid is desirable from the standpoint of economic efficiency. The concentration of the acid is preferably 0.1 to 100 wt % and more preferably 0.5 to 15 wt %. The reaction temperature can be 100 to 300° C. and the reaction time can be 1 second to 60 minutes. Large amounts of monosaccharide comprising a component derived from hemicellulose as a main component obtained by hydrolysis and its oligosaccharide are contained in the liquid component after the acid treatment. Particularly when treatment with concentrated sulfuric acid of 50% or more and more preferably 80% or more is performed, both hemicellulose and cellulose are hydrolyzed and the hydrolysis treatment can be performed by one stage. In further hydrolyzing with saccharifying enzyme after the acid treatment, a solid component and a liquid component obtained after the acid treatment are separated and each may be subjected to the hydrolysis, or a mixture of the solid component and the liquid component may be directly subjected to the hydrolysis. The acid used is contained in the solid component and liquid component obtained by the acid treatment. Therefore, to perform the hydrolysis reaction by saccharifying enzyme, it is preferred that an acid-treated product is previously neutralized.

The alkali treatment is a treatment method of reacting the cellulose-containing biomass with an alkali aqueous solution, specifically an aqueous solution of a hydroxide salt (excluding ammonium hydroxide). By the alkali treatment, lignin inhibiting a reaction of cellulose and hemicellulose by saccharifying enzyme can be mainly removed. The hydroxide salt used is preferably sodium hydroxide or calcium hydroxide. The concentration of the alkali aqueous solution is preferably 0.1 to 60 wt %, and it is added to the cellulose-containing biomass to perform treatment at a temperature of generally 100 to 200° C. and preferably 110 to 180° C. The number of the treatment is not particularly limited, and the treatment may be conducted one time or several times. When the treatment is conducted two or more times, each treatment may be conducted under different conditions. Pretreated product obtained by the alkali treatment contains an alkali. Therefore, when further conducting hydrolysis by saccharifying enzyme, it is preferred that the pretreated product is previously neutralized.

The ammonia treatment is a treatment method of reacting an ammonia aqueous solution or 100% ammonia (liquid or gas) with a cellulose-derived biomass, and the method described in JP-A-2008-161125 or JP-A-2008-535664 can be used. In the ammonia treatment, crystallinity of cellulose is broken by reacting ammonia with a cellulose component and, as a result, reaction efficiency with saccharifying enzyme is considerably improved. In general, ammonia is added to a cellulose-containing biomass such that the concentration is 0.1 to 15 wt % based on the cellulose-containing biomass, and the biomass is treated at 4 to 200° C. and preferably 60 to 150° C. The number of the treatment is not particularly limited, and the treatment may be conducted one time or several times. In further subjecting the pretreated product obtained by the ammonia treatment to a hydrolysis reaction by saccharifying enzyme, it is preferred that neutralization of ammonia or removal of ammonia is previously conducted.

The hydrothermal treatment is a treatment method of treating the cellulose-containing biomass with pressurized hot water of 100 to 400° C. for 1 second to 60 minutes. The treatment is generally conducted such that the concentration of the cellulose-containing biomass that is insoluble in water at an ordinary temperature of 25° C. after the treatment is 0.1 to 50 wt % based on the total weight of the cellulose-containing biomass and water. The pressure depends on the treatment temperature and is therefore not particularly limited. However, the pressure is preferably 0.01 to 10 MPa. In the hydrothermal treatment, elution components into hot water differ by the temperature of pressurized hot water. In general, when the temperature of pressurized hot water is increased, a first group of tannin and lignin first elutes off from the cellulose-containing biomass, next a second group of hemicellulose elutes off at 140 to 150° C. or higher, and then a third group of cellulose elutes off at a temperature exceeding about 230° C. Furthermore, a hydrolysis reaction of hemicellulose and cellulose may occur simultaneous with the eluting off. To improve the reaction efficiency of saccharifying enzyme to cellulose and hemicellulose by utilizing the difference in elution components by the temperature of pressurized hot water, multistage treatment may be conducted changing the treatment temperature. Of fractions obtained by the hydrothermal treatment, a water-soluble substance containing components eluted into pressurized hot water is called a hot water-soluble substance, and a substance excluding the hot water-soluble substance is called a hot water-insoluble substance.

The hot water-insoluble substance is a solid component mainly containing a cellulose (C6) component of disaccharide or more, obtained as a result that much of lignin and hemicellulose component has been eluted off. Other than cellulose as the main component, a hemicellulose component and a lignin component are sometimes contained. The content ratio of those components varies depending on the temperature of pressurized hot water of the hydrothermal treatment and the kind of the biomass to be treated. Water content of the hot water-insoluble substance is 10% to 90% and more preferably 20% to 80%.

The hot water-soluble substance is a water-soluble substance containing hemicellulose, lignin, tannin and a part of a cellulose component that have eluted into pressurized hot water that is a liquid state or a slurry state, and is a liquid state or a slurry state. The hot water-soluble substance contains much polysaccharide, oligosaccharide and monosaccharide that have been hydrolyzed.

Pretreatment such as a grinding treatment of mechanically cutting fibers using a cutter mill, a hammer mill or the like, a pulverization treatment using a ball mill, a jet mill or the like, a wet treatment using a grinder, a mechanochemical treatment or a steaming and blasting treatment of steaming by steam for a short time and instantly releasing a pressure for blasting by volume expansion may be carried out before the hydrolysis treatment method described above. The reason for this is that by crushing, exposed area of cellulose and hemicellulose is increased and the efficiency of the hydrolysis reaction by saccharifying enzyme is increased.

The saccharifying enzyme is preferably cellobiohydrolase and xylanase that are an enzyme component contained in crude cellulase derived from filamentous fungi.

The cellobiohydrolase is a general term of an enzyme releasing cellobiose by hydrolysis of cellulose chains, and enzymes belonging to cellobiohydrolase are described as EC number: EC3.2.1.91.

The xylanase is a general term of an enzyme having the characteristic of acting to xylan that is a main component constituting xylan, and enzymes belonging to xylanase are described as EC number: EC3.2.1.8.

Examples of filamentous fungi include microorganisms such as *Trichoderma*, *Aspergillus*, *Cellulomonas*, *Chlostridium*, *Streptomyces*, *Humicola*, *Acremonium*, *Irpex*, *Mucor* and *Talaromyces*. Of those filamentous fungi, *Trichoderma* produces a large amount of enzyme components having high specific activity in a culture medium in the hydrolysis of cellulose and is therefore preferably used.

*Trichoderma* microorganisms are not particularly limited, and examples thereof include microorganisms derived from *Trichoderma reesei* QM9414, *Trichoderma reesei* QM9123, *Trichoderma reesei* RutC-30, *Trichoderma reesei* PC3-7, *Trichoderma reesei* CL-847, *Trichoderma reesei* MCG77, *Trichoderma reesei* MCG80 and *Trichoderma viride* QM9123. Of those *Trichoderma* microorganisms, *Trichoderma reesei* is preferred. Microorganisms derived from *Trichoderma reesei* described above may be mutants in which productivity of cellulase has been improved by applying a mutation treatment with a mutagen, ultraviolet irradiation or the like.

Crude cellulase preferably contains enzyme components other than the above-described cellobiohydrolase and xylanase from the standpoints of the improvement of hydrolysis efficiency of a cellulose-based biomass pretreated product and the improvement of the yield of xylooligosaccharide. As an enzyme component of crude cellulase, other than the cellobiohydrolase and xylanase, at least one enzyme component selected from the group consisting of endoglucanase and β-glucosidase, preferably at least one enzyme component selected from the group consisting of endoglucanase, β-glucosidase, arabinofuranosidase, xylan esterase and ferulic acid esterase, and more preferably at least one enzyme component selected from the group consisting of endoglucanase, β-glucosidase, arabinofuranosidase, xylan esterase, ferulic acid esterase, mannanase and mannosidase is preferably contained.

The weight ratio of each enzyme component of crude cellulase is not particularly limited. However, for example, 50 to 95 wt % of cellobiohydrolase is contained in a culture medium derived from *Trichoderma reesei*, and endoglucanase, β-glucosidase, xylanase, β-xylosidase and the like are contained in the remaining components. *Trichoderma* microorganisms produce strong cellulase component in a culture medium, but on the other hand, β-glucosidase is held in the cell or on the surface layer of the cell and as a result, β-glucosidase activity in the culture medium is low. Therefore, a product obtained by further adding the same kind or different kind of β-glucosidase to the culture medium derived from *Trichoderma reesei* is preferably used as the crude cellulase. β-Glucosidase derived from *Aspergillus* can be preferably used as the different kind of β-glucosidase. Example of β-glucosidase derived from *Aspergillus* includes Novozyme 188 commercially available from Novozymes A/S. Furthermore, a culture medium having improved β-glucosidase activity obtained by introducing a gene in *Trichoderma* microorganisms and culturing *Trichoderma* microorganisms genetically modified to produce in the culture medium may be used as crude cellulase.

For the crude cellulase, for example, filamentous fungus culture medium exemplified above, a culture supernatant obtained by removing cell body from the culture medium or a culture medium containing a pulverized product of cell body of microorganisms may be directly used, or products obtained by concentrating those may be used as the crude cellulase. Examples of the method of removing cell bodies from a culture medium include centrifugation, filter pressing and a microfiltration membrane treatment. Those methods can be used alone or as a combination thereof. As a method of obtaining a pulverized product of cell bodies of microorganisms, the pulverized product of cell bodies can be obtained by suspending cell body separated by the method such as centrifugation in a buffer solution and pulverizing the cell bodies by an ultrasonic homogenizer or a beads type homogenizer. In using concentrated crude cellulase, examples of the method for concentration include concentration methods by evaporative concentration or an ultrafiltration membrane treatment. Also, enzymes are purified by the conventional method and added to crude cellulase to prepare a mixture, the resulting mixture is formed into a preparation, and the preparation may be used as the crude cellulase. For purification of enzymes, the conventional method such as ammonium sulfate fractionation or column chromatography can be used. When a product obtained by adding purified enzymes to a filamentous fungus culture medium is used as the crude cellulase, the purified enzymes are added in an amount of protein not exceeding the amount of protein in a culture supernatant before adding the purified enzymes. Furthermore, when a preparation is used as crude cellulase, a preparation having a substance other than enzyme such as a protease inhibitor, a dispersant, a dissolution accelerator or a stabilizer may be used as crude cellulase.

The crude cellulase may be prepared by heat-treating, at specific pH and temperature, a filamentous fungus culture medium, a culture supernatant in which cell body has been removed from a culture medium, a culture medium containing a pulverized product of cell body of microorganisms, or a preparation obtained by purifying enzymes by the conventional method, adding the purified enzymes to crude cellulase and combining those. In this case, the crude cellulase diluted with an aqueous solvent is heat-treated at specific pH and temperature conditions for a certain period of time. The concentration of enzymes at the heat treatment, in terms of protein concentration, is 0.01 to 10 wt %, more preferably 0.1 to 5 wt % and still more preferably 0.2 to 1 wt %. When the protein concentration at the heat treatment is less than 0.1 wt %, the stability of the major part of the enzyme components in the crude cellulase is deteriorated and many enzyme components are deactivated during the heat treatment. As a result, hydrolysis efficiency of cellulose-based biomass pretreated product is decreased and the yield of xylooligosaccharide is decreased. When the protein concentration exceeds 5 wt %, stability of protein is increased, enzyme activity decomposing xylooligosaccharide in the crude cellulase into xylose is difficult to decrease, and then the yield of xylooligosaccharide is decreased.

In the hydrolysis reaction using saccharifying enzyme of crude cellulase, the solid component concentration of cellulose-based biomass pretreated product is 1 to 30 wt %, preferably 3 to 20 wt % and still more preferably 5 to 10 wt %. The hydrolysis reaction using saccharifying enzyme is conducted at pH in the vicinity of preferably 3.0 to 8.0 and more preferably 5.5 to 8.0. The hydrolysis reaction using saccharifying enzyme is conducted in a range of preferably 1 to 144 hours, more preferably 3 to 72 hours and still more preferably 6 to 24 hours. Also it is preferred that solid-liquid separation is conducted to remove undecomposed solid components at the completion of hydrolysis by saccharifying enzyme. The method of removing solid components includes a centrifugation method, a membrane separation method and the like, but is not particularly limited. Plural kinds of those solid-liquid separations may be combined and used.

In the sugar aqueous solution obtained by the hydrolysis step of the cellulose-containing biomass, solid components and water-soluble polymers such as tannin, saccharifying enzyme or protein component derived from biomass are preferably removed before passing them through a separation membrane having a molecular weight cut-off of 300 to 800 to prevent clogging or fouling in conducting a filtration treatment by a separation membrane having a molecular weight cut-off of 300 to 800 in a post-stage treatment. The method of removing those components is not particularly limited, but the preferred removal method includes a method of filtering a sugar aqueous solution by passing through a microfiltration membrane and/or an ultrafiltration membrane having a molecular weight cut-off larger than 2,000 and filtering off solid components and water-soluble polymers to the non-permeation side. The filtration method includes pressure filtration, vacuum filtration and centrifugal filtration, but is not particularly limited. The filtration operation is roughly classified into constant pressure filtration, constant flow rate filtration and non-constant pressure and non-constant flow rate filtration, but is not particularly limited. The filtration operation may be a multistage filtration that uses a microfiltration membrane or an ultrafiltration membrane having molecular weight cut-off of larger than 2,000 at two or more times to efficiently remove solid components.

The microfiltration membrane is a membrane having an average pore diameter of 0.01 μm to 5 mm, is abbreviated as a microfiltration membrane, MF membrane or the like and is preferably used when removing solid components contained in the sugar aqueous solution. The microfiltration membrane used herein may be an inorganic membrane and may be an organic membrane. Examples thereof include organic materials such as cellulose, cellulose ester, polysulfone, polyether sulfone, chlorinated polyethylene, polypropylene, polyolefin, polyvinyl alcohol, polymethyl methacrylate, polyvinylidene fluoride and polytetrafluoroethylene; metals such as stainless steel; and inorganic materials such as ceramics.

The ultrafiltration membrane means a separation membrane having a molecular weight cut-off of 600 to 200,000 and is abbreviated as an ultrafiltration membrane, UF membrane or the like. As described in The Membrane Society of Japan, hymenology experiment series, Vol. III, artificial membrane, editorial committee members/Naofumi Kimura, Sin-ichi Nakao, Haruhiko Oya and Tsutomu Nakagawa (Kyoritu Shuppan Co., Ltd., 1993), page 92 that "A curve obtained by plotting data on a graph having a horizontal axis of a molecular weight of a solute and a vertical axis of a rejection is called a molecular-cut-off curve. Molecular weight at which a rejection is 90% is called a molecular weight cut-off of a membrane.", the molecular weight cut-off is known to one skilled in the art as an index showing membrane performance of an ultrafiltration membrane. The ultrafiltration membrane having a molecular weight cut-off of larger than 2,000 is used, thereby water-soluble polymers, particularly saccharifying enzyme, contained in the sugar aqueous solution can be suitably removed.

The material of the ultrafiltration membrane is not particularly limited, but examples thereof include organic materials such as cellulose, cellulose ester, polysulfone, sulfonated polysulfone, polyether sulfone, sulfonated polyether sulfone, chlorinated polyethylene, polypropylene, polyolefin, polyvinyl alcohol, polymethyl methacrylate, polyvinylidene fluoride and polytetrafluoroethylene; metals such as stainless steel; and inorganic materials such as ceramics. Above all, an organic membrane is preferable because of removability of hydrophobic substances. Of those, polyether sulfone is preferred and sulfonated polyether sulfone is more preferred.

The form of the ultrafiltration membrane used is not particularly limited and may be any of a spiral type, a hollow fiber type, a tubular type and a flat membrane type.

Specific examples of the ultrafiltration membrane include G-5 type, GH type and GK type of DESAL; SPE1 of Synder; PM1000, PM2000, MPS-36 and SR2 manufactured by KOCH; GR95Pp and ETNA01PP manufactured by ALFA-LAVAL, and NTR-7450 (molecular weight cut-off: 600 to 800, see Water Research 37 (2003), 864 to 872) and NTR-7410 (molecular weight cut-off: 1,000 to 2,000, see Sanitary Engineering Symposium Academic Papers, 5, 246-251 (1997)) manufactured by Nitto Denko Corporation.

Filtration pressure in the filtration treatment by the ultrafiltration membrane is preferably 0.1 MPa or more and 8 MPa or less, although depending on the concentration of the sugar aqueous solution. When the filtration pressure is lower than 0.1 MPa, membrane permeation rate may decrease and when the filtration pressure is higher than 8 MPa, the pressure may affect damage of the membrane. Furthermore, when the pressure is 0.5 MPa or more and 6 MPa or less, permeation flux of the membrane is high and as a result, the sugar aqueous solution can be efficiently permeated and this is more preferred.

The permeation flux of the membrane in the filtration treatment by the ultrafiltration membrane is preferably 0.2 m/D or more and 4.0 m/D or less. When the permeation flux is 0.2 m/D or less, concentration by the ultrafiltration membrane is not performed and when the permeation flux is 2.0 m/D or less, fouling of the membrane becomes remarkable. Furthermore, when the permeation flux is 0.5 m/D or more and 2.0 m/D or more, the filtration by the ultraviolet membrane becomes easy to perform, and this is more preferred.

The pH of the sugar aqueous solution in the filtration treatment by the ultrafiltration membrane is not particularly limited, but the pH is preferably 5 or less and more preferably 4 or less. When the pH is 1 or less, a large amount of an acid is required when adjusting pH. Therefore, the lower limit of pH is preferably 1 from the standpoint of economic efficiency. The effect of the pH adjustment of the sugar aqueous solution is remarkable when a substance that is an aromatic compound such as coumaric acid or ferulic acid and has a carboxylic acid group is contained.

Our methods are characterized in that the obtained sugar aqueous solution is subjected to the filtration treatment by a separation membrane having a molecular weight cut-off of 300 to 800 and preferably 300 to 500 and/or 600 to 800. In the filtration treatment by a separation membrane having a molecular weight cut-off of less than 300 or more than 800, catalyst poisons inhibiting a sugar alcohol synthesis step described after cannot be separated and this is not preferred. The filtration treatment by a separation membrane may be a filtration treatment by a plurality of separation membranes, and in the filtration treatment by a plurality of separation membranes, may be a filtration treatment by a single kind of separation membranes and may be a filtration treatment by a plural kinds.

The material of the separation membrane is not particularly limited, and a polymer material such as cellulose ester polymer such as cellulose acetate, polyamide, polyester, polyimide or vinyl polymer can be used. However, the separation membrane is not limited to a membrane constituted of a single kind of the above materials, but may be a membrane containing a plurality of membrane materials. The membrane structure may be either of an asymmetric membrane having a dense layer on at least one surface thereof and having micropores with a pore size gradually increasing toward the inside of the membrane or another surface from the dense layer, and a composite membrane having a very thin functional layer formed on a dense layer of an asymmetric membrane by other materials.

Of those, a composite membrane with a functional layer of polyamide, having high pressure resistance, high water permeability, high solute removing performance, and excellent potential, is preferred. To keep durability to operation pressure, high water permeability and rejection performance, a membrane having a structure in which a functional layer comprises polyamide and is maintained by a support comprising a porous membrane or a non-woven fabric is suitable.

Specific examples of a preferred polyamide separation membrane include NFW series manufactured by SYNDER.

The filtration pressure in the filtration treatment by the above-described separation membrane is preferably 0.1 MPa or more and 8 MPa or less, although depending on the concentration of the sugar aqueous solution. When the filtration pressure is lower than 0.1 MPa, the membrane permeation rate is decreased and when the filtration pressure is higher than 8 MPa, it may affect the damage of the membrane. When the filtration pressure is 0.5 MPa or more and 6 MPa or less, the membrane permeation flux is high and as a result, the sugar aqueous solution can be efficiently permeated and this is more referred.

Our methods are characterized in that catalyst poisons of the metal catalyst used in a post-stage hydrogenation reaction are removed from the non-permeation side of the separation membrane while collecting the sugar solution from the permeation side of the separation membrane by the filtration treatment.

Regarding catalyst poisons removed from the non-permeation side of the separation membrane, specific substances are not yet specified. However, it is believed that they are substances generated by hydrolysis of a cellulose-containing biomass and are substances having a molecular weight exceeding at least 300. Low molecular weight organic substances such as a nitrogen compound, a sulfur compound and a phosphorus compound, and metals such as Ag, Hg, Pb, Bi, Sn, Cd and As have conventionally been known as catalyst poisons of a metal catalyst. However, those conventional catalyst poisons are substances having a molecular weight smaller than 300 to 800, and there is a possibility that catalyst poisons generated by hydrolysis of a cellulose-containing biomass are novel catalyst poisons that are not identified so far.

Sugars which are starting materials in the production of sugar alcohol by a post-stage hydrogenation reaction are contained in the sugar solution collected from the permeation side of the separation membrane. The kind of sugars is not particularly limited, but it is preferred that monosaccharide is a main component and it is preferred that xylose and/or glucose are a main component.

Our methods are characterized in that the sugar solution obtained by the above-described step is subjected to a hydrogenation reaction to synthesize sugar alcohol. In the hydrogenation reaction, a liquid phase containing sugar is brought into contact with a metal catalyst in the presence of hydrogen. In this case, the metal catalyst may be suspended in the liquid phase (suspension method) or the liquid phase may be passed through a fluidized catalyst bed (fluidized bed method) or a fixed catalyst bed (fixed bed method).

The metal catalyst used in the hydrogenation reaction is preferably a catalyst containing metals selected from elements of Group 8 in the periodic table. The elements of Group 8 in the periodic table mean iron, cobalt, nickel and platinum group elements. The platinum group elements mean 6 elements of ruthenium, rhodium, palladium, osmium, iridium and platinum. Of the metals selected from elements of Group 8 in the periodic table, metals selected from nickel and platinum group elements are more preferred and ruthenium or nickel is still more preferred. Specific examples of the metal catalyst containing ruthenium or nickel include a ruthenium catalyst and Raney nickel catalyst.

The ruthenium content in the ruthenium catalyst is preferably 0.1 to 5 wt % and more preferably 1 to 5 wt %, based on the weight of a carrier material, in terms of ruthenium element.

The Raney nickel catalyst is a catalyst obtained by activating Raney alloy comprising nickel and aluminum as main components in an alkali aqueous solution, and other metals may be added to the above metals for the purpose of increasing hydrogenation activity and imparting durability against poisonous substances. The metal added is at least one selected from iron, chromium, cobalt, manganese and molybdenum. The Raney nickel catalyst may be an activated Raney nickel catalyst. Specifically, the Raney nickel catalyst is R-2313A type catalyst available from Nikko Rica Corporation. The R-2313A type catalyst is a co-catalyst of molybdenum and generally contains about 1.5% of molybdenum and 85% of nickel.

When the Raney nickel catalyst is used, it is preferred that a basic compound is added to adjust pH of a reaction liquid to 7 to 10 to prevent melting of nickel. The pH is more preferably 8 to 9. The basic compound added is at least one selected from the group consisting of magnesium oxide, sodium borate, potassium borate and dipotassium hydrogen phosphate.

The concentration of sugars in the sugar solution supplied to the hydrogenation reaction is not particularly limited and can basically be freely selected. The concentration of sugars is wt % calculated based on the value obtained by dividing the total weight (hereinafter referred to as sugar weight) of glycose, xylose and oligosaccharide by the total weight of the solution, and in many cases, is 2 to 80 wt % and preferably 20 to 70 wt %.

The reaction solvent in the hydrogenation reaction is an aqueous solvent. The term "aqueous" means water and a mixture of water containing preferably at least one water-miscible organic solvent in an amount of 50 vol % or less, preferably 50 vol % or less and particularly 50 vol % or less. The mixture is, for example, a mixture of C1 to C4 alkanol such as methanol, ethanol, n-propanol or isopropanol, and water. Water is used as a single solvent in many cases.

Isopropanol is a donor of a hydrogen atom, and it is assumed that a hydrogen transfer reaction proceeds to an aldehyde of sugar. Therefore, it is preferred to use isopropanol in that the yield of sugar alcohol as a product is further improved.

Hydrogen partial pressure in the hydrogenation reaction is preferably 0.1 to 15 MPa, more preferably 1 to 10 MPa and still more preferably 1 to 5 MPa. The reaction temperature is preferably 80 to 200° C. and more preferably 100 to 150° C.

For the weight of the sugar solution as a starting material, a sugar weight W1 is regarded as a conversion weight, and the relationship between W1 and ruthenium catalyst amount W2 in terms of ruthenium is not particularly limited. However, a ratio of W1 to W2 (W1/W2) is preferably 1 to 100 and more preferably 1 to 20, from the standpoint of excellent economic efficiency together with excellent yield of a product.

For the weight of the sugar solution as a starting material, a sugar weight W1 is regarded as a conversion weight, and the relationship between W1 and Raney nickel catalyst amount W3 in terms of nickel is not particularly limited. However, a ratio of W1 to W3 (W1/W3) is preferably 1 to 100 and more preferably 1 to 20, from the standpoint of excellent economic efficiency together with excellent yield of a product.

The metal catalyst supported on a solid carrier may be used. It is appropriate that the solid carrier supporting the metal catalyst is a solid carrier in which at least a part thereof comprises a porous material and it is appropriate that a transition metal is supported on the surface of the porous material. Therefore, in the solid carrier used for the catalyst, it is appropriate that the surface of at least the part thereof on which the transition metal is supported comprises a porous material. The whole solid carrier may comprise a porous material or the surface of the support comprising a non-porous material may be covered with a porous material. Furthermore, the support may comprise other porous material.

The solid carrier is, for example, that at least a part thereof can comprise an inorganic oxide. The inorganic oxide is preferably the above-described porous material. The solid carrier used for the catalyst is preferably that at least a part thereof is a solid carrier indicating acidity, and solid carrier indicating acidity is preferably the above-described porous material. The solid carrier is preferably a solid carrier in which hydrogen molecules dissociate by a metal such as Pt to develop proton acid points on the carrier.

Specific examples of the solid carrier include silica, alumina, silica-alumina, zeolite, titania, zirconia and activated carbon.

The shape and form of the solid carrier are not particularly limited, and the solid carrier can have, for example, a powder form, a particulate form, a granular form, a pellet form, a honeycomb form, an extrusion type, a ring form, a columnar form, a rib extrusion type and a rib ring form. The powder form, particle form, granular form and pellet form carriers can comprise only, for example, the above-described porous material, an oxide or a material indicating acidity. On the other hand, the honeycomb structure carrier may be a carrier, in which the surface of a support comprising a non-porous material, for example, cordierite or the like is covered with the above-described porous material, an oxide or a material indicating acidity. Furthermore, the support may comprise other porous material as described above.

Hydrogenation by a suspension method and an apparatus suitable for the hydrogenation by a fluidized catalyst bed and a fixed catalyst bed are known from the prior arts (for example, Ullmanns Enzyklopadie der Techenischen Chemie (Ullmann's Encyclopedia of Industrial Chemistry), 4th Edition, Volume, 13, pp. 135 et seq, and P. N. Rylander, "Hydrogenation and Dehydrogenation" in Ullman's Encyclopedia of Industrial Chemistry, 5th, CD-ROM).

The obtained sugar alcohol is not particularly limited, but the sugars contained in the sugar solution are used as a starting material, it is preferred that a reduced product of a monosaccharide is a main component and it is preferred that xylitol and/or sorbitol are a main component.

To achieve quality to an extent such that the sugar alcohol can be used in general food and drink, as necessary, the sugar alcohol obtained by the hydrogenation reaction is purified by a method such as deionization by an ion-exchange resin or the like, adjustment of the content by chromatographic separation or the like, and as necessary, is further passed through operations of concentration; powdering by spray drying, granulation drying or the like; molding; and the like. Thus, products of various forms such as a liquid product, a powdered product, a granular product, a molded product, a mixture with other components and the like can be obtained.

The obtained sugar alcohol can be used alone as a sweetener. Furthermore, an appropriate amount of the sugar alcohol is mixed with at least one of various sugars and sugar alcohols such as sugar, grape sugar, glucose, xylose, lactose, honey, powder candy, isomerized sugar, maltose, maltooligosaccharide, xylooligosaccharide, cellooligosaccharide, glutinous starch syrup, trehalose, cellobiose, palatinose, maple sugar, erythritol, xylitol, mannitol, sorbitol, maltitol, lactitol, maltotetraitol, xylobiitol, xylotriitol, xylotetraitol, reduced palatinose, reduced starch hydrolysate, reduced malt sugar syrup and reduced xyloorigosaccharide; various high sweeteners such as stevioside, dihydrochalcone, glycyrrhizin, saccharin, aspartame and sucralose; and sweeteners including such as Siraitia grosvenorii extract, glycin and alanine, in an optional proportion, and the resulting mixture can be used. Furthermore, the sugar alcohol is mixed with various starches and processed starches such as starch, oxidized starch, acid-treated starch, processed starch, dextrin, branched dextrin, cyclodextrin, branched cyclodextrin, hydrides of various dextrins and polydextrolose, and the resulting mixture can be used.

Other than the above, the sugar alcohol can be used in cigarettes, toothpaste, lipstick, lip cream, internal medicine, troche, cod-liver oil drops, mouth fresheners, mouth flavoring agent, mouthwash and the like, the shape can be selected depending on uses such as a solid shape, a powder shape, a granular shape, a paste shape or a liquid shape. The sugar alcohol can also be used as taste improvers and quality improvers to luxury goods, cosmetics, pharmaceuticals and the like.

Various derivatives such as ether derivatives and ester derivatives can be significantly easily produced by a chemical reaction using the sugar alcohol as a raw material.

The obtained sugar alcohol can also produce polyol derivatives such as ethylene glycol, propylene glycol, 1,3-propanediol, glycerol and anhydrous sugar alcohol. Those sugar alcohol derivatives can be used in a surfactant, an emulsifier, a reagent for an enzyme reaction, plastics, a synthetic base of chemical fibers and the like.

Preferred examples of the anhydrous sugar alcohol which is polyol derivatives include mixtures comprising sorbitan and/or xylitan as a main component.

The sorbitan is a general term of 1,4-anhydro-D-sortitol, 1,5-anhydro-D-sorbitol, 2,5-anhydro-D-sorbitol, 3,6-anhydro-D-sorbitol, 2,5-anhydro-L-mannitol, 2,5-anhydro-L-iditol and the like, and the sorbitan may be a single substance of the above-described components and may be a mixture of the above-described components (Applied Catalysis, A: General 492 (2015) 252-261).

Xylitan is a general term of 1,4-anhydro-D-xylitol, 2,5-anhydro-D-xylitol and the like, and the xylitan may be a single substance of the above-described components and may be a mixture of the above-described components (Energy & Fuels, 29 (10) 6529-6535; 2015).

The anhydrous sugar alcohol is obtained by thermally dehydrating the sugar alcohol in the presence of an acid catalyst.

The acid catalyst is preferably an organic acid, an inorganic acid and Lewis acid, and more preferably an organic acid such as methanesulfonic acid, p-toluenesulfonic acid, benzensulfonic acid, trifluromethanesulfonic acid, acetic acid, trifluoroacetic acid, trichloroacetic acid or citric acid; an inorganic acid such as hydrochloric acid, concentrated sulfuric acid, sodium sulfate, nitric acid, phosphoric acid, phosphorous acid, oxalic acid, boric acid or fluoroboric acid; and Lewis acid such as iron chloride, aluminum chloride or bismuth triflate. The acid catalyst is more preferably p-toluenesulfonic acid, methanesulfonic acid, concentrated sulfuric acid and iron chloride.

The sugar alcohol concentration in the synthesis of the anhydrous sugar alcohol is not particularly limited. The sugar alcohol concentration is wt % calculated based on the value obtained by dividing the total weight (hereinafter referred to as sugar alcohol weight) of sorbitol, xylitol and oligosaccharide alcohol by the total weight of the solution and in many cases, is 50 to 80 wt %, preferably 55 to 80 wt % and more preferably 60 to 80 wt %. The reaction solvent is an aqueous solvent or the absence of a solvent and is preferably the absence of a solvent.

The reaction pressure is preferably 5 to 300 Pa and more preferably 10 to 150 Pa.

The reaction temperature is preferably 100 to 200° C., more preferably 100 to 160° C. and still more preferably 120 to 140° C.

The reaction time is preferably 0.5 to 2 hours and more preferably 0.8 to 1.2 hours, at the temperatures described above.

When the reaction time is too short, reaction conversion is decreased. When the reaction time is too long, excessive dehydration reaction of sorbitol proceeds and isosorbide is formed, both resulting in deterioration of yield of sorbitan. Therefore, the reaction time is preferably 0.5 to 2 hours and more preferably 0.8 to 1.2 hours.

For the weight of sugar alcohol as a starting material, a sugar alcohol weight W4 is regarded as a conversion weight, and the relationship to an acid catalyst amount W5 is that when a ratio (W4/W5) between W4 and W5 is too large, reaction conversion is decreased and when the ratio is too small, excessive dehydration reaction of sorbitol proceeds and isosorbide is formed, both resulting in deterioration of yield of sorbitan. Therefore, the W4/W5 is preferably 75 to 200 and more preferably 100 to 150.

The obtained anhydrous sugar alcohol is that sorbitan and/or xylitan as main components thereof are known for use as a moisturizing agent, and therefore can be used, for example, in lotions, creams, milky lotions, skin lotions, beauty liquids, gels, pack preparations or the like. Furthermore, the anhydrous sugar alcohol can be used in skin care preparations such as body lotions or facial cleaners, makeup preparations, hair care preparations, hand soaps, soaps, hand sanitizers or bath additives. Additionally, the anhydrous sugar alcohol can be used by blending with pharmaceuticals, quasi-drugs and cosmetics, and is particularly easily applied to external agent compositions applied to an outer skin such as pharmaceuticals, quasi-drugs or cosmetic compositions.

The obtained anhydrous sugar alcohol is condensed with fatty acid, and then can be used in surfactants, reagents for an enzyme reaction, and the like. Furthermore, PEG obtained by adding polyethylene glycol chains to a condensate of fatty acid ester and anhydrous sugar alcohol can be used in surfactants, reagents for an enzyme reaction, and the like.

The fatty acid is not particularly limited, and examples thereof include linear or branched saturated fatty acid and unsaturated fatty acid having 6 to 24 carbon atoms. Specific examples of the fatty acid include caproic acid, caprylic acid, capric acid, lauric acid, myristic acid, palmitic acid, stearic acid, behenic acid, lignoceric acid, oleic acid, elaidic acid, linoleic acid, linolenic acid, erucic acid, isostearic acid, 2-ethylhexyl acid and condensed ricinoleic acid. Those fatty acids can be used alone or in combination of two or more kinds.

The charged amount of the fatty acid to sugar alcohol or anhydrous sugar alcohol varies depending on the target degree of esterification and is not uniform. The content of unreacted sugar alcohol or anhydrous sugar alcohol in the reaction product obtained increases as the degree of esterification is small. Therefore, our methods can become particularly effective, for example, when reacting in the charged amount of fatty acid of about 0.1 to 1 mol per 1 mol of sugar alcohol or anhydrous sugar alcohol.

The esterification reaction between sugar alcohol or anhydrous sugar alcohol and fatty acid may be conducted in the absence of a catalyst or may be conducted using an acid catalyst or an alkali catalyst. The reaction is preferably conducted in the presence of an alkali catalyst. Examples of the acid catalyst include proton acid such as sulfuric acid, phosphoric acid, phosphorous acid, hypophosphorous acid, p-toluenesulfonic acid or methanesulfonic acid, and salts and metal halides of those. Examples of the alkali catalyst include an alkali metal hydroxide such as sodium hydroxide, potassium hydroxide or lithium hydroxide, an alkali metal carbonate such as sodium carbonate or potassium carbonate, an alkali metal hydrogen carbonate, an alkali metal, alkaline earth metal, an alkaline earth metal oxide, alkaline earth metal hydroxide, other metals and oxides of the other metals. The amount of the alkali catalyst used is 0.01 to 10.0 mass % and preferably 0.1 to 1.0 mass %, of the total charged amount (in terms of a dried matter).

The esterification reaction is conducted, for example, by supplying sugar alcohol or anhydrous sugar alcohol, fatty acid and a catalyst to a usual reaction vessel equipped with a stirrer, a heating jacket, a baffle plate, an inert gas blowing tube, a thermometer and a water separator equipped with a condenser, followed by stirring and mixing, and heating the resulting mixture at a predetermined temperature for a certain period of time in an optional inert gas atmosphere such as nitrogen or carbon dioxide while removing water produced by the esterification reaction to the outside of the system. The reaction temperature is usually 150 to 250° C. and preferably 200 to 250° C. The reaction pressure condition is reduced pressure or atmospheric pressure, and the reaction time is 0.5 to 15 hours and preferably 1 to 6 hours. The end point of the reaction is generally determined by measuring an acid value of a reaction mixture, with a standard being 10 or less.

The reaction pressure is preferably 5 to 300 Pa and more preferably 10 to 150 Pa.

After completion of the esterification reaction, when a catalyst has been used, the catalyst remained in the reaction mixture is neutralized. In such a case, it is preferred to conduct a neutralization treatment at a liquid temperature of 180 to 200° C. When sodium hydroxide is used as an alkali catalyst and neutralized with phosphoric acid (85 mass %), the neutralization of the catalyst is conducted by adding phosphoric acid (85 mass %) in at least an amount obtained by dividing the amount of phosphoric acid calculated by neutralization formula (1) by 0.85, preferably 2 to 3 times amount of phosphoric acid (85 mass %) of the amount obtained by dividing the amount of phosphoric acid calculated by neutralization formula (1) by 0.85, to a reaction mixture and sufficiently mixing the resulting mixture. After the neutralization, the mixture is allowed to stand at that temperature for preferably 0.5 hours or more and more preferably 1 to 10 hours. When unreacted sugar alcohol or anhydrous sugar alcohol is separated into a lower layer, the lower layer is removed.

 Neutralization formula (1):

The obtained anhydrous sugar alcohol ester comprises sorbitan ester and/or xylitan ester as a main component, and the sorbitan ester is widely used as an emulsifier of industrial products such as plastic, rubber, fiber and paint; pharmaceuticals; and cosmetics, including foods. Therefore, the application as the same uses is assumed.

The obtained sugar alcohol can produce polyol derivatives such as ethylene glycol, propylene glycol, 1,3-propane diol, glycerol and anhydrous sugar. Those sugar alcohol derivatives can also be used in a surfactant, an emulsifier, a reagent for enzyme reaction, plastic and a synthetic base of chemical fiber.

Those sugar alcohol derivatives can also be used in a surfactant, an emulsifier, a reagent for enzyme reaction, plastic and a synthetic base of chemical fiber.

EXAMPLES

Our methods are described below in more detail by reference to the following Examples. However, the scope of this disclosure is not limited by the Examples.

Reference Example 1: Preparation of Trichoderma-Derived Crude Cellulase

Trichoderma-derived crude cellulase was prepared by the following method.
Precultivation
5% (w/vol) corn steep liquor, 2% (w/vol) glucose, 0.37% (w/vol) ammonium tartarate, 0.14% (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid and 0.0026% (w/vol) hexaammonium heptamolybdate tetrahydrate were added to distilled water, and 100 mL of the resulting solution was placed in 500 mL Erlenmeyer flask equipped with baffle and subjected to autoclave sterilization at 121° C. for 15 minutes. After cooling, PE-M and Tween 80 separately subjected to autoclave sterilization at 121° C. for 15 minutes were added in an amount of 0.01% (w/vol), respectively, to the solution. Trichoderma reesei ATCC66589 (furnished from ATCC) was inoculated in the preculture medium to be 1×10$^5$ count/mL, and was cultured by shaking at 28° C. for 72 hours in 180 rpm to perform precultivation (shaking apparatus: BIO-SHAKER BR-40LF, manufactured by TAITEC).

Cultivation

A 5% (w/vol) corn steep liquor, 2% (w/vol) glucose, 10% (w/vol) cellulose (AVICEL), 0.37% (w/vol) ammonium tartarate, 0.14% (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid and 0.0026% (w/vol) hexaammonium heptamolybdate tetrahydrate were added to distilled water, and 2.5 L of the resulting solution was placed in 5 L stirring jar (DPC-2A, manufactured by ABLE Corporation) and subjected to autoclave sterilization at 121° C. for 15 minutes. After cooling, PE-M and Tween 80 separately subjected to autoclave sterilization at 121° C. for 15 minutes were added in an amount of 0.1%, respectively, to the solution. 250 mL of Trichoderma reesei PC3-7 previously precultivated in a liquid culture by the method described above was inoculated in the solution obtained above. Thereafter, cultivation was conducted at 28° C. for 87 hours in 300 rpm and an air flow rate of 1 vvm. After centrifugation, the supernatant was subjected to membrane filtration (STERICUP GV, material: PVDF, manufactured by MILLIPORE). β-Glucosidase (Novozyme 188) was added to the culture medium prepared under the conditions described above in an amount of 1/100 as protein weight ratio to prepare crude cellulase.

Reference Example 2: Hydrolysis Step of Cellulose-Containing Biomass (Diluted Sulfuric Acid Treatment and Saccharifying Enzyme Treatment)

Rice straw was used as a cellulose-containing biomass. The cellulose-containing biomass was dipped in 1% sulfuric acid aqueous solution and treated in an autoclave (manufactured by Nitto Koatsu) at 150° C. for 30 minutes. After the treatment, solid-liquid separation was conducted to separate into a sulfuric acid aqueous solution and sulfuric acid-treated cellulose. The sulfuric acid-treated cellulose and diluted sulfuric acid treatment liquid were stirred and mixed such that the solid component concentration was 10 wt %, and pH was adjusted to near 7.0 by sodium hydroxide. Trichoderma reesei-derived crude cellulase as a saccharifying enzyme was added to the mixed liquid, and hydrolysis reaction was conducted at 40° C. for 1 day while mixing the mixed liquid by stirring. Thereafter, centrifugation (3000G)

was conducted and undecomposed cellulose or lignin was removed by separation. Thus, a sugar aqueous solution was obtained.

Reference Example 3: Pretreatment of Cellulose-Containing Biomass (Steaming and Blasting Treatment and Saccharifying Enzyme Treatment)

Rice straw was used as a cellulose-containing biomass. 100 g of the cellulose-containing biomass was placed in a 2 liter steaming and blasting testing machine (manufactured by Nihon Dennetsu Co., Ltd.) and steam was then blown thereto. The inside of the vessel was maintained under 2.5 MPa for 2.5 minutes, and then instantaneously exposed to the atmosphere to perform a blasting treatment, and a sample was collected. The temperature inside the vessel at this time was 225° C. Water content of the treated product at this time was 84.4%. Water was added such that the solid component concentration is 10 wt %, and 1N sodium hydroxide aqueous solution was added to adjust pH to 7.0. Trichoderma reesei-derived crude cellulase as a saccharifying enzyme was added to the resulting mixed liquid, and hydrolysis reaction was conducted at 40° C. for 1 day while stirring and mixing. Thereafter, the reaction mixture was subjected to centrifugation (3000G) to separate and remove undecomposed cellulose and lignin. Thus, a sugar aqueous solution was obtained.

Reference Example 4: Hydrolysis Step of Cellulose-Containing Biomass (Hydrothermal Treatment and Saccharifying Enzyme Treatment)

Rice straw was used as a cellulose-containing biomass. The cellulose-containing biomass was dipped in water, and treated in an autoclave (manufactured by Nitto Koatsu Co., Ltd.) at 180° C. for 20 minutes while stirring. The pressure in this case was 10 MPa. After the treatment, the treated mixture was subjected to solid-liquid separation by centrifugation (3000G) to separate into a solution component and a treated biomass component. The pH of the solution was adjusted to near 7.0 by sodium hydroxide. Trichoderma reesei-derived crude cellulase as a saccharifying enzyme was added to the resulting mixed liquid, and hydrolysis reaction was conducted at 40° C. for 1 day while stirring and mixing. Thereafter, the reaction mixture was subjected to centrifugation (3000G) to separate and remove undecomposed cellulose or lignin. Thus, a sugar aqueous solution was obtained.

Reference Example 5: Hydrolysis Step of Cellulose-Containing Biomass (Ammonia Treatment and Saccharifying Enzyme Treatment)

Rice straw was used as a cellulose-containing biomass. The cellulose-containing biomass was placed in a small-sized reactor (TVS-N2, 30 ml, manufactured by Taiatsu Techno Corporation) and cooled with liquid nitrogen. Ammonia gas having 100% concentration was flown into the reactor and the sample was completely dipped in 100% liquid ammonia. The lid of the reactor was closed, and the reactor was left at room temperature for about 15 minutes. Then, the reactor was treated in an oil bath of 150° C. for 1 hour. After the treatment, the reactor was taken out of the oil bath, ammonia gas was immediately leaked in a draft chamber, and the inside of the reactor was vacuumed to 10 Pa by a vacuum pump to dry the cellulose-containing biomass. Pure water and the treated cellulose-containing biomass were stirred and mixed such that a solid component centration is 15 wt %, and the pH was adjusted to near 7.0 by sulfuric acid and by sodium oxide. Trichoderma reesei-derived crude cellulase as a saccharifying enzyme was added to the resulting mixed liquid, and hydrolysis reaction was conducted at 40° C. for 1 day while stirring and mixing. Thereafter, the reaction mixture was subjected to centrifugation (3000G) to separate and remove undecomposed cellulose or lignin. Thus, a sugar aqueous solution was obtained.

Reference Example 6: Hydrolysis Step of Cellulose-Containing Biomass (Sodium Hydroxide Treatment and Saccharifying Enzyme Treatment)

Rice straw was used as a cellulose-containing biomass. The cellulose-containing biomass was dipped in a sodium hydroxide aqueous solution such that the amount of the alkali added is 10 wt % based on the cellulose-containing biomass, and the resulting mixture was treated in an autoclave (manufactured by Nitto Koatsu Co., Ltd.) at 80° C. for 3 hours. After the treatment, the treated mixture was subjected to solid-liquid separation to separate into a sodium hydroxide aqueous solution and a sodium hydroxide-treated cellulose. Then, the sodium hydroxide-treated cellulose and the sodium hydroxide treating liquid were stirred and mixed such that the solid component concentration is 10 wt %, and the pH was then adjusted to near 7 by hydrochloric. Trichoderma reesei-derived crude cellulase as a saccharifying enzyme was added to the resulting mixed liquid, and hydrolysis reaction was conducted at 40° C. for 1 day while stirring and mixing. Thereafter, the reaction mixture was subjected to centrifugation (3000G) to separate and remove undecomposed cellulose or lignin. Thus, a sugar aqueous solution was obtained.

Reference Example 7: Microfiltration Membrane and Ultrafiltration Membrane Treatment of Sugar Aqueous Solution Each of the sugar aqueous solutions described in Reference Examples 2 to 6 was filtered using a microfiltration membrane (product name: Slurry Cap, pore size: 0.45 m). The permeate of the microfiltration membrane was then filtered using an ultrafiltration membrane and a flat membrane filtration unit "SEPA-11" (manufactured by GE Osmonics Inc.) under the conditions of membrane surface line speed: 20 cm/sec and filtration pressure: 1 MPa, and the filtration treatment was conducted until a permeation flux reaches 0.5 m/day. Thus, a permeate was obtained. The ultrafiltration membrane used was "M-U1812" (manufactured by Applied Membrane Inc., material: polyether sulfone, molecular weight cut-off: 10000).

Reference Example 8: Measurement of Sugar Concentration

Concentrations of glucose, xylose, xylobiose and xylotriose in the sugar solution were quantitatively analyzed based on a calibration curve prepared by samples of glucose, xylose, xylobiose and xylotriose under the following conditions using Hitachi high performance liquid chromatography "LaChrom Eite" (HITACHI):
Column: KS802, KS803 (Shodex)
Mobile phase: Water
Detection method: RI
Flow rate: 0.5 mL/min
Temperature: 75° C.

Example 1: Filtration Treatment Using Separation Membrane Having Molecular Weight Cut-Off of 300 to 500

The permeate obtained by microfiltration membrane and ultrafiltration membrane treatment of the sugar aqueous solution described in Reference Example 7 was concentrated until flux reaches 0.5 m/D, under the conditions of membrane surface line speed: 20 cm/sec and filtration pressure: 4 MPa using a filtration membrane having a molecular weight cut-off of 300 to 500 and a flat membrane filtration unit "SEPA-11" (manufactured by GE Osmonics Inc.), and RO water in an amount of 3 times was added. The concentration and the addition of RO water were repeated 2 times in the same manners as above. Thereafter, concentration was conducted until a permeation flux reaches 0.5 m/day, and the filtration treatment of the non-permeate containing catalyst poisons and the permeate was conducted. This Example can be applied to the permeate obtained by the microfiltration membrane and ultrafiltration membrane treatment described in Reference Example 7 of any of the sugar aqueous solutions of Reference Examples 2 to 5.

Example 2: Reverse Osmosis Membrane Treatment of Permeate of Separation Membrane Having Molecular Weight Cut-Off of 300 to 500

All permeates of the separation membrane described in Example 1 were combined and filtered under the conditions of membrane surface line speed: 20 cm/sec and filtration pressure: 1 MPa using a reverse osmosis membrane and a flat membrane filtration unit "SEPA-11" (manufactured by GE Osmonics Inc.), and the filtration treatment was conducted until permeation flux reaches 0.5 m/day. The reverse osmosis membrane used was "FRH-2514" (manufactured by ROPUR, material: crosslinked all aromatic polyamide, NaCl rejection: 99%, molecular weight cut-off: 100 or less). The permeate obtained was concentrated to Bri ×74 under reduced pressure, and a sugar solution was obtained. Compositions of the sugar solution obtained are shown in Table 1. This Example can be applied to the permeates obtained according to Reference Example 7 and Example 1 using any of sugar aqueous solutions of Reference Examples 2 to 5 as a raw material, and the sugar solution can be similarly obtained.

TABLE 1

| | Solution composition (wt %) |
|---|---|
| Glucose | 43 |
| Xylose | 10 |
| Xylobiose | 7 |
| Xylotriose | 1 |
| Water | 30 |
| Other | 9 |

Example 3: Filtration Treatment Using Separation Membrane Having Molecular Weight Cut-Off of 600 to 800

The permeate obtained by microfiltration membrane and ultrafiltration membrane treatment of the sugar aqueous solution described in Reference Example 7 was concentrated until flux reaches 0.5 m/D, under the conditions of membrane surface line speed: 20 cm/sec and filtration pressure: 4 MPa using a separation membrane having a molecular weight cut-off of 600 to 800 and a flat membrane filtration unit "SEPA-11" (manufactured by GE Osmonics Inc.), and RO water in an amount of 3 times was added. The concentration and the addition of RO water were repeated 2 times in the same manners as above. Thereafter, concentration was conducted until a permeation flux reaches 0.5 m/day, the filtration treatment of the non-permeate containing catalyst poisons and the permeate was conducted, and the permeate was collected. The separation membrane used was "1812F" (manufactured by SYNDER, material: polyamide, molecular weight cut-off: 600 to 800). This Example can be applied to the permeate obtained by the microfiltration membrane and ultrafiltration membrane treatment described in Reference Example 7 of any of the sugar aqueous solutions of Reference Examples 2 to 5.

Example 4: Reverse Osmosis Membrane Treatment of Permeate of Separation Membrane Having Molecular Weight Cut-Off of 600 to 800

All permeates of the separation membrane described in Example 3 were combined and filtered under the conditions of membrane surface line speed: 20 cm/sec and filtration pressure: 1 MPa using a reverse osmosis membrane and a flat membrane filtration unit "SEPA-11" (manufactured by GE Osmonics Inc.), and the filtration treatment was conducted until a permeation flux reaches 0.5 m/day. The reverse osmosis membrane used was "FRH-2514" (manufactured by ROPUR, material: crosslinked all aromatic polyamide, NaCl rejection: 99%, molecular weight cut-off: 100 or less). The permeate obtained was concentrated, and a permeate was obtained. The permeate obtained was concentrated to Bri ×74 under reduced pressure, and a sugar solution was obtained. Compositions of the sugar solution obtained are shown in Table 2. This Example can be applied to the permeates obtained according to Reference Example 7 and Example 3 using any of sugar aqueous solutions of Reference Examples 2 to 5 as a raw material, and the sugar solution can be similarly obtained.

TABLE 2

| | Solution composition (wt %) |
|---|---|
| Glucose | 43 |
| Xylose | 8 |
| Xylobiose | 7 |
| Xylotriose | 2 |
| Water | 29 |
| Other | 11 |

Example 5: Investigations of Hydrogenation Reaction of Sugar Solution Using Raney Nickel Catalyst Raney nickel catalyst (manufactured by Nikko Rica Corporation, R-2313A, 4 mg) and ion-exchanged water (20 mL) were added to the sugar solution (400 mg) described in Example 2, and the resulting mixture was subjected to a hydrogenation reaction at a temperature of 100° C. under a hydrogen pressure of 5 MPa. Thirty minutes later, the reaction mixture was cooled to room temperature, and after substituting the inside of the system with nitrogen, glucose, xylose, sorbitol and xylitol in the reaction liquid were quantified by the quantitative method of sugars described in Reference Example 8. As a result of calculating molar yield of sorbitol from glucose and molar yield of xylitol from xylose each, sorbitol was 55% and xylitol was 90% (Table 3). When the same operation as in this Example is carried out using any of the sugar solutions of Reference Examples 2 to 5 as a raw material, the sugar alcohol can be similarly obtained. Example 6: Investigations of hydrogenation reaction of sugar solution using 5% activated carbon-supported ruthenium catalyst (Ru/C catalyst).

Example 6: Investigations of Hydrogenation Reaction of Sugar Solution Using 5% Activated Carbon-Supported Ruthenium Catalyst (Ru/C Catalyst)

5% Ru/C (manufactured by N. E. CHEMCAT Corporation, AC-4503, 4 mg) and ion-exchanged water (20 mL) were added to the sugar solution (399 mg) described in Example 2, and the resulting mixture was subjected to a hydrogenation reaction at temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the molar yield was calculated. As a result, sorbitol was 52% and xylitol was 88% (Table 3). When the same operation as in this Example is carried out using any of sugar solutions of Reference Examples 2 to 5 as a raw material, the sugar alcohol can be similarly obtained.

Example 7: Investigations of Hydrogenation Reaction of Sugar Solution Using Raney Nickel Catalyst Raney nickel catalyst (manufactured by Nikko Rica Corporation, R-2313A, 4 mg) and ion-exchanged water (20 mL) were added to the sugar solution (400 mg) described in Example 4, and the resulting mixture was subjected to a hydrogenation reaction at a temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the molar yield was calculated. As a result, sorbitol was 41% and xylitol was 84% (Table 3). When the same operation as in this Example is carried out using any of sugar solutions of Reference Examples 2 to 5 as a raw material, the sugar alcohol can be similarly obtained.

Example 8: Investigations of Hydrogenation Reaction of Sugar Solution Using 5% Activated Carbon-Supported Ruthenium Catalyst (Ru/C Catalyst)

5% Ru/C (manufactured by N. E. CHEMCAT Corporation, AC-4503, 4 mg) and ion-exchanged water (20 mL) were added to the sugar solution (399 mg) described in Example 4, and the resulting mixture was subjected to a hydrogenation reaction at temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the molar yield was calculated. As a result, sorbitol was 38% and xylitol was 79% (Table 3). When the same operation as in this Example is carried out using any of sugar solutions of Reference Examples 2 to 5 as a raw material, the sugar alcohol can be similarly obtained.

Comparative Example 1: Investigations of Hydrogenation Reaction of Catalyst Poison-Containing Sugar Solution Using Raney Nickel Catalyst The non-permeate of separation membrane containing catalyst poison (201 mg) described in Example 1, Raney nickel catalyst (manufactured by Nikko Rica Corporation, R-2313A, 4 mg) and ion-exchanged water (20 mL) were added to the sugar solution (202 mg) described in Example 2, and the resulting mixture was subjected to a hydrogenation reaction at temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the molar yield was calculated. As a result, sorbitol was 7% and xylitol was 27% (Table 3). Because the Raney nickel catalyst was poisoned by catalyst poisons contained in the non-permeate described in Example 1, the yield was remarkably decreased. When the same operation as in this Comparative Example is carried out using any of sugar solutions of Reference Examples 2 to 5 as a raw material, the molar yield is similarly decreased.

Comparative Example 2: Investigations of Hydrogenation Reaction of Catalyst Poison-Containing Sugar Solution Using 5% Ru/C Catalyst The separation membrane concentrate containing catalyst poison (201 mg) described in Example 1, 5% Ru/C (manufactured by N. E. CHEMCAT Corporation, AC-4503, 4 mg) and ion-exchanged water (20 mL) were added to the sugar solution (202 mg) described in Example 2, and the resulting mixture was subjected to a hydrogenation reaction at temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the molar yield was calculated. As a result, sorbitol was 7% and xylitol was 27% (Table 3). Because the ruthenium catalyst was poisoned by catalyst poisons contained in the concentrate described in Example 1, the yield was remarkably decreased. When the same operation as in this Comparative Example is carried out using any of sugar solutions of Reference Examples 2 to 5 as a raw material, the molar yield is similarly decreased.

Comparative Example 3: Investigations of Hydrogenation Reaction by Raney Nickel Catalyst after Poisoning Raney nickel catalyst (manufactured by Nikko Rica Corporation, R-2313A, 4 mg) used in Comparative Example 1 was cleaned with ion-exchanged water (50 mL), collected, and then again added to the sugar solution (202 mg) described in Example 2. After diluting with ion-exchanged water (20 mL), the resulting mixture was subjected to a hydrogenation reaction at temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the molar yield was calculated. As a result, sorbitol was 6% and xylitol was 25% (Table 3). Therefore, activity of the Raney nickel catalyst poisoned in Comparative Example 1 was not recovered even though cleaning operation was conducted, and the molar yield remained decreased. Even though the same operation as in this Comparative Example is carried out using any of sugar solutions of Reference Examples 2 to 5 as a raw material, the molar yield is similarly decreased.

Comparative Example 4: Investigations of Hydrogenation Reaction by 5% Ru/C Catalyst after Poisoning 5% Ru/C (manufactured by N. E. CHEMCAT Corporation, AC-4503, 4 mg) used in Comparative Example 2 was cleaned with ion-exchanged water (50 mL), collected, and then again added to the sugar solution (202 mg) described in Example 2. After diluting with ion-exchanged water (20 mL), the resulting mixture was subjected to a hydrogenation reaction at temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the yield was calculated. As a result, sorbitol was 7% and xylitol was 25% (Table 3). Therefore, activity of the ruthenium catalyst poisoned in Comparative Example 2 was not recovered even though cleaning operation was conducted, and the molar yield remained decreased. Even though the same operation as in this Comparative Example is carried out using any of sugar solutions of Reference Examples 2 to 5 as a raw material, the molar yield is similarly decreased.

Comparative Example 5: Investigations of Hydrogenation Reaction of Catalyst Poison-Containing Sugar Solution Using Raney Nickel Catalyst The non-permeate of separation membrane containing catalyst poison (201 mg) described in Example 2, Raney nickel catalyst (manufactured by Nikko Rica Corporation, R-2313A, 4 mg) and ion-exchanged water (20 mL) were added to the sugar solution (202 mg) described in Example 4, and a hydrogenation reaction was conducted at a temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the molar yield was calculated. As a result, sorbitol was 13% and xylitol was 53% (Table 3). Because the Raney nickel catalyst was poisoned by catalyst poisons contained in the non-permeate described in Example 1, the yield was remarkably decreased. When the same operation as in this Comparative Example is carried out using any of sugar solutions of Reference Examples 2 to 5 as a raw material, the molar yield is similarly decreased.

Comparative Example 6: Investigations of Hydrogenation Reaction of Catalyst Poison-Containing Sugar Solution Using 5% Ru/C Catalyst The separation membrane concentrate containing catalyst poison (201 mg) described in Example 3, 5% Ru/C (manufactured by N. E. CHEMCAT Corporation, AC-4503, 4 mg) and ion-exchanged water (20 mL) were added to the sugar solution (202 mg) described in Example 4, and a hydrogenation reaction was conducted at a temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the molar yield was calculated. As a result, sorbitol was 13% and xylitol was 55% (Table 3). Because the ruthenium catalyst was poisoned by catalyst poisons contained in the concentrate described in Example 1, the molar yield was remarkably decreased. When the same operation as in this Comparative Example is carried out using any of sugar solutions of Reference Examples 2 to 5 as a raw material, the molar yield is similarly decreased.

Comparative Example 7: Investigations of Hydrogenation Reaction by Raney Nickel Catalyst after Poisoning Raney nickel catalyst (manufactured by Nikko Rica Corporation, R-2313A, 4 mg) used in Comparative Example 6 was cleaned with ion-exchanged water (50 mL), collected, and then again added to the sugar solution (202 mg) described in Example 4. After diluting with ion-exchanged water (20 mL), the resulting mixture was subjected to a hydrogenation reaction at temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the yield was calculated. As a result, sorbitol was 12% and xylitol was 54% (Table 3). Therefore, activity of the Raney nickel catalyst poisoned in Comparative Example 1 was not recovered even though cleaning operation was conducted, and the molar yield remained decreased. When the same operation as in this Comparative Example is carried out using any of sugar solutions of Reference Examples 2 to 5 as a raw material, the molar yield is similarly decreased.

Comparative Example 8: Investigations of Hydrogenation Reaction by 5% Ru/C Catalyst after Poisoning 5% Ru/C (manufactured by N. E. CHEMCAT Corporation, AC-4503, 4 mg) used in Comparative Example 5 was cleaned with ion-exchanged water (50 mL), collected, and then again added to the sugar solution (202 mg) described in Example 4. After diluting with ion-exchanged water (20 mL), the resulting mixture was subjected to a hydrogenation reaction at temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the yield was calculated. As a result, sorbitol was 14% and xylitol was 53% (Table 3). Therefore, activity of the ruthenium catalyst poisoned in Comparative Example 2 was not recovered even though cleaning operation was conducted, and the molar yield remained decreased. When the same operation as in this Comparative Example is carried out using any of sugar solutions of Reference Examples 2 to 5 as a raw material, the molar yield is similarly decreased.

Comparative Example 9: Investigations of Hydrogenation Reaction of Ultrafiltration Membrane Permeate Using Raney Nickel Catalyst Raney nickel catalyst (manufactured by Nikko Rica Corporation, R-2313A, 4 mg) and ion-exchanged water (20 mL) were added to the ultrafiltration membrane permeate (402 mg) described in Reference Example 7, and the resulting mixture was subjected to a hydrogenation reaction at temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the yield was calculated. As a result, sorbitol was 28% and xylitol was 71%. The molar yield was decreased by catalyst poisons which remained through the ultrafiltration membrane treatment (Table 3). When the same operation as in this Comparative Example is carried out using any of sugar solutions of Reference Examples 2 to 5 as a raw material, the molar yield is similarly decreased.

Comparative Example 10: Investigations of Hydrogenation Reaction of Ultrafiltration Membrane Permeate Using 5% Ru/C Catalyst 5% Ru/C (manufactured by N. E. CHEMCAT Corporation, AC-4503, 4 mg) and ion-exchanged water (20 mL) were added to the ultrafiltration membrane permeate (402 mg) described in Reference Example 7, and the resulting mixture was subjected to a hydrogenation reaction at temperature of 100° C. under a hydrogen pressure of 5 MPa. Thirty minutes later, the reaction mixture was cooled to room temperature, and after substituting the inside of the system with nitrogen, the reaction liquid was quantified in the same manner as in Example 5 and the molar yield was calculated. As a result, sorbitol was 23% and xylitol was 66%. The molar yield was decreased by catalyst poisons which remained through the ultrafiltration membrane treatment (Table 3). When the same operation as in this Comparative Example is carried out using any of sugar solutions of Reference Examples 2 to 5 as a raw material, the yield is similarly decreased.

TABLE 3

| Example | Temperature (° C.) | Pressure (MPa) | Catalyst | Molar yield (%) Sorbitol | Xylitol |
|---|---|---|---|---|---|
| Ex. 5 | 100 | 5 | Ra—Ni | 55 | 90 |
| Ex. 6 | | | 5% Ru/C | 52 | 88 |
| Ex. 7 | | | Ra—Ni | 41 | 84 |
| Ex. 8 | | | 5% Ru/C | 38 | 79 |
| Comp. EX. 1 | | | Ra—Ni | 7 | 25 |
| Comp. EX. 2 | | | 5% Ru/C | 7 | 27 |
| Comp. EX. 3 | | | Ra—Ni | 6 | 25 |
| Comp. EX. 4 | | | 5% Ru/C | 7 | 25 |
| Comp. EX. 5 | | | Ra—Ni | 13 | 53 |
| Comp. EX. 6 | | | 5% Ru/C | 13 | 55 |
| Comp. EX. 7 | | | Ra—Ni | 12 | 54 |
| Comp. EX. 8 | | | 5% Ru/C | 14 | 53 |
| Comp. EX. 9 | | | Ra—Ni | 28 | 71 |
| Comp. EX. 10 | | | 5% Ru/C | 23 | 66 |

Example 9: Investigations of Thermal Dehydration at Reaction Temperature of 140° C. Using Raw Material Having Sugar Alcohol Concentration of 80%

Raney nickel catalyst (manufactured by Nikko Rica Corporation, R-2313A, 4 mg) and ion-exchanged water (20 mL) were added to the sugar solution (200 mg) described in Example 2, and the resulting mixture was subjected to a hydrogenation reaction at temperature of 100° C. under a hydrogen pressure of 5 MPa. Three hours later, the reaction mixture was cooled to room temperature, and after substituting the inside of the system with nitrogen, glucose, xylose, sorbitol and xylitol in the reaction liquid were quantified by the quantification method described in Reference Example 8, the molar yield of sorbitol from glucose and the molar yield of xylitol from xylose were calculated each. As a result, sorbitol was 99% and xylitol was 99%. The reaction liquid was filtered through celite and then concentrated into the liquid having a sugar alcohol concentration of 80% under reduced pressure. After heating to 140° C., concentrated sulfuric acid (manufactured by Kanto Chemical Co., Inc., special grade, 2 mg) was added and the pressure was reduced to 300 Pa. After stirring the resulting mixture at 140° C. for 1 hour, the mixture was cooled to room temperature and the pressure was returned to atmospheric pressure. After diluting using ion-exchanged water (10 mL), analysis was conducted by the analysis method described in Reference Example 8, the molar yields of sorbitan and isosorbide from sorbitol and the molar yield of xylitan from xylitol were calculated each. As a result, sorbitan was 73%, isosorbide was 13% and xylitan was 99% (Table 4). When the same operation as in this Example is carried out using any of sugar solutions of Reference Examples 2 to 5 as a raw material, anhydrous sugar alcohol can be similarly obtained.

Example 10: Investigations of Thermal Dehydration at Reaction Temperature of 150° C. Using Raw Material Having Sugar Alcohol Concentration of 80%

Raney nickel catalyst (manufactured by Nikko Rica Corporation, R-2313A, 4 mg) and ion-exchanged water (20 mL) were added to the sugar solution (200 mg) described in Example 2, and the resulting mixture was subjected to a hydrogenation reaction at temperature of 100° C. under a hydrogen pressure of 5 MPa. Three hours later, the reaction mixture was cooled to room temperature, and after substituting the inside of the system with nitrogen, glucose, xylose, sorbitol and xylitol in the reaction liquid were quantified by the quantification method described in Reference Example 8. The molar yield of sorbitol from glucose and the molar yield of xylitol from xylose were calculated each. As a result, sorbitol was 99% and xylitol was 99%. The reaction liquid was filtered through celite and then concentrated into the liquid having a sugar alcohol concentration of 80% under reduced pressure. After heating to 150° C., concentrated sulfuric acid (manufactured by Kanto Chemical Co., Inc., special grade, 2 mg) was added and the pressure was reduced to 300 Pa. After stirring the resulting mixture at 150° C. for 1 hour, the mixture was cooled to room temperature and the pressure was returned to atmospheric pressure. After diluting using ion-exchanged water (10 mL), analysis was conducted by the analysis method described in Reference Example 8, the molar yields of sorbitan and isosorbide from sorbitol and the molar yield of xylitan from xylitol were calculated each. As a result, sorbitan was 63%, isosorbide was 27% and xylitan was 99% (Table 4). When the same operation as in this Example is carried out using any of sugar solutions of Reference Examples 2 to 5 as a raw material, anhydrous sugar alcohol can be similarly obtained.

Example 11: Investigations of Thermal Dehydration at Reaction Temperature of 160° C. Using Raw Material Having Sugar Alcohol Concentration of 80%

Raney nickel catalyst (manufactured by Nikko Rica Corporation, R-2313A, 4 mg) and ion-exchanged water (20 mL) were added to the sugar solution (200 mg) described in Example 2, and the resulting mixture was subjected to a hydrogenation reaction at temperature of 100° C. under a hydrogen pressure of 5 MPa. Three hours later, the reaction mixture was cooled to room temperature, and after substituting the inside of the system with nitrogen, glucose, xylose, sorbitol and xylitol in the reaction liquid were quantified by the quantification method described in Reference Example 8, the molar yield of sorbitol from glucose and the molar yield of xylitol from xylose were calculated each. As a result, sorbitol was 99% and xylitol was 99%. The reaction liquid was filtered through celite and then concentrated into the liquid having sugar alcohol concentration of 80% under reduced pressure. After heating to 160° C., concentrated sulfuric acid (manufactured by Kanto Chemical Co., Inc., special grade, 2 mg) was added and the pressure was reduced to 300 Pa. After stirring the resulting mixture at 160° C. for 1 hour, the mixture was cooled to room temperature and the pressure was returned to atmospheric pressure. After diluting using ion-exchanged water (10 mL), analysis was conducted by the analysis method described in Reference Example 8, the molar yields of sorbitan and isosorbide from sorbitol and the molar yield of xylitan from xylitol were calculated each. As a result, sorbitan was 70%, isosorbide was 7% and xylitan was 99% (Table 4). When the same operation as in this Example is carried out using any of sugar solutions of Reference Examples 2 to 5 as a raw material, anhydrous sugar alcohol can be similarly obtained.

TABLE 4

| Example | Solvent | Temperature (° C.) | Time (hour) | Molar yield (%) | | |
| --- | --- | --- | --- | --- | --- | --- |
| | | | | Sorbitan | Isosorbide | Xylitan |
| Ex. 9 | 80% aqueous solution | 140 | 1 | 73 | 13 | 99 |
| Ex. 10 | | 150 | | 63 | 27 | 99 |
| Ex. 11 | | 160 | | 37 | 53 | 99 |
| Ex. 12 | 60% aqueous solution | 140 | 5 | 70 | 7 | 99 | reaction liquid was filtered through celite and then concentrated into the liquid having sugar alcohol concentration of 80% under reduced pressure. After heating to 160° C., concentrated sulfuric acid (manufactured by Kanto Chemical Co., Inc., special grade, 2 mg) was added and the pressure was reduced to 300 Pa. After stirring the resulting mixture at 160° C. for 1 hour, the mixture was cooled to room temperature and the pressure was returned to atmospheric pressure. After diluting using ion-exchanged water (10 mL), analysis was conducted by the analysis method described in Reference Example 8, the molar yields of sorbitan and isosorbide from sorbitol and the molar yield of xylitan from xylitol were calculated each. As a result, sorbitan was 37%, isosorbide was 53% and xylitan was 99% (Table 4). When the same operation as in this Example is carried out using any of sugar solutions of Reference Examples 2 to 5 as a raw material, anhydrous sugar alcohol can be similarly obtained.

Example 12: Investigations of Thermal Dehydration at Reaction Temperature of 140° C. Using Raw Material Having Sugar Alcohol Concentration of 60%

Raney nickel catalyst (manufactured by Nikko Rica Corporation, R-2313A, 4 mg) and ion-exchanged water (20 mL) were added to the sugar solution (200 mg) described in Example 2, and the resulting mixture was subjected to a hydrogenation reaction at temperature of 100° C. under a hydrogen pressure of 5 MPa. Three hours later, the reaction mixture was cooled to room temperature, and after substituting the inside of the system with nitrogen, glucose, xylose, sorbitol and xylitol in the reaction liquid were quantified by the quantification method described in Reference Example 8, the molar yield of sorbitol from glucose and the molar yield of xylitol from xylose were calculated each. As a result, sorbitol was 99% and xylitol was 99%. The reaction liquid was filtered through celite and then concentrated into the liquid having sugar alcohol concentration of 60% under reduced pressure. After heating to 140° C., concentrated sulfuric acid (manufactured by Kanto Chemical Co., Inc., special grade, 2 mg) was added and the pressure was reduced to 300 Pa. After stirring the resulting mixture at 140° C. for 5 hour, the mixture was cooled to room temperature and the pressure was returned to atmospheric pressure. After diluting using ion-exchanged water (10 mL), analysis was conducted by the analysis method described in Reference Example 8, the molar yields of sorbitan and isosorbide from sorbitol and the molar yield of xylitan from xylitol were calculated each. As a result, sorbitan was 70%, isosorbide was 7% and xylitan was 99% (Table 4). When the same operation as in this Example is carried out using any of sugar solutions of Reference Examples 2 to 5 as a raw material, anhydrous sugar alcohol can be similarly obtained.

Example 13: Production of Sorbitan/Xylitan Lauric Acid Ester Mixture

The anhydrous sugar alcohol solution described in Example 7 was dehydrated at 75° C. under a reduced pressure of 400 Pa for 10 minutes. 212 mg (1.3 mmol) of lauric acid (manufactured by Kanto Chemical Co., Inc.) was charged, 5.4 mg (0.1 mmol) of sodium hydroxide as a catalyst was added, and an esterification reaction was conducted at 200° C. under atmospheric pressure for 6 hours in nitrogen gas stream until an acid value reaches 10 or less. The reaction mixture obtained was cooled to 180° C. and 39.4 mg of phosphoric acid (85 mass %) was added to neutralize the catalyst, thereby obtaining sorbitan/xylitan lauric acid ester mixture (311 mg). The mixture had an acid value of 3.3 and a hydroxyl value of 220 (Table 5). When the same operation as in this Example is carried out using any of sugar solutions of Reference Examples 2 to 5 as a raw material, anhydrous sugar alcohol can be similarly obtained.

Example 14: Production of Sorbitan/Xylitan Palmitic Acid Ester Mixture

The anhydrous sugar alcohol solution described in Example 7 was dehydrated at 75° C. under a reduced pressure of 400 Pa for 10 minutes. 344 mg (1.3 mmol) of palmitic acid (manufactured by Kanto Chemical Co., Inc.) was charged, 5.4 mg (0.1 mmol) of sodium hydroxide as a catalyst was added, and an esterification reaction was conducted at 200° C. under atmospheric pressure for 6 hours in nitrogen gas stream until an acid value reaches 10 or less. The reaction mixture obtained was cooled to 180° C. and 39.4 mg of phosphoric acid (85 mass %) was added to neutralize the catalyst, thereby obtaining sorbitan/xylitan palmitic acid ester mixture (392 mg). The mixture had an acid value of 3.8 and a hydroxyl value of 250 (Table 5). When the same operation as in this Example is carried out using any of sugar solutions of Reference Examples 2 to 5 as a raw material, anhydrous sugar alcohol can be similarly obtained.

Example 15: Production of Sorbitan/Xylitan Stearic Acid Ester Mixture

The anhydrous sugar alcohol solution described in Example 7 was dehydrated at 75° C. under a reduced pressure of 400 Pa for 10 minutes. 381 mg (1.3 mmol) of stearic acid (manufactured by Kanto Chemical Co., Inc.) was charged, 5.4 mg (0.1 mmol) of sodium hydroxide as a catalyst was added, and an esterification reaction was conducted at 200° C. under atmospheric pressure for 6 hours in nitrogen gas stream until an acid value reaches 10 or less. The reaction mixture obtained was cooled to 180° C. and 39.4 mg of phosphoric acid (85 mass %) was added to neutralize the catalyst, thereby obtaining sorbitan/xylitan stearic acid ester mixture (392 mg). The mixture had an acid value of 3.1 and a hydroxyl value of 210 (Table 5). When the same operation as in this Example is carried out using any of sugar solutions of Reference Examples 2 to 5 as a raw material, anhydrous sugar alcohol can be similarly obtained.

Example 16: Production of Sorbitan/Xylitan Oleic Acid Ester Mixture

The anhydrous sugar alcohol solution described in Example 7 was dehydrated at 75° C. under a reduced pressure of 400 Pa for 10 minutes. 381 mg (1.3 mmol) of oleic acid (manufactured by Kanto Chemical Co., Inc.) was charged, 5.4 mg (0.1 mmol) of sodium hydroxide as a catalyst was added, and an esterification reaction was conducted at 200° C. under atmospheric pressure for 6 hours in nitrogen gas stream until an acid value reaches 10 or less. The reaction mixture obtained was cooled to 180° C. and 39.4 mg of phosphoric acid (85 mass %) was added to neutralize the catalyst, thereby obtaining sorbitan/xylitan oleic acid ester mixture (392 mg). The mixture had an acid value of 3.7 and a hydroxyl value of 240 (Table 5). When the same operation as in this Example is carried out using any of sugar solutions of Reference Examples 2 to 5 as a raw material, anhydrous sugar alcohol can be similarly obtained.

TABLE 5

| Example | Fatty acid | Acid value (mgKOH/g) | Hydroxyl value (mgKOH/g) |
|---|---|---|---|
| Ex. 13 | Lauric acid | 3.3 | 220 |
| Ex. 14 | Palmitic acid | 3.8 | 250 |
| Ex. 15 | Stearic acid | 3.1 | 210 |
| Ex. 16 | Oleic acid | 3.7 | 240 |

INDUSTRIAL APPLICABILITY

Sugar alcohol can be produced in high yield by filtering a sugar aqueous solution obtained by a hydrolysis treatment of a cellulose-containing biomass through a separation membrane having a molecular weight cut-off of 300 to 800 to remove catalyst poisons to the non-permeation side, collecting a sugar solution from the permeation side, and subjecting the sugar solution obtained to hydrogenation in the presence of a metal catalyst. Furthermore, anhydrous sugar alcohol can be produced in high yield by acting an acid catalyst to sugar alcohol, thereby performing thermal dehydration. Additionally, an anhydrous alcohol ester can be produced by heating the anhydrous sugar alcohol in the presence of fatty acid and a solid base.

The invention claimed is:

1. A method of producing a sugar alcohol from a cellulose-containing biomass as a raw material, comprising:
    step (1): a step of filtering a sugar aqueous solution obtained by hydrolysis of the cellulose-containing biomass through a separation membrane having a molecular weight cut-off of 300 to 500 to remove a catalyst poison to a non-permeation side and collecting a sugar solution from a permeation side; and
    step (2): a step of subjecting the sugar solution obtained in the step (1) to a hydrogenation reaction in the presence of a metal catalyst.

2. The method according to claim 1, wherein the metal catalyst in the step (2) is a ruthenium catalyst or a Raney nickel catalyst.

3. The method according to claim 1, wherein the sugar alcohol comprises sorbitol and/or xylitol as a main component.

4. A method of producing an anhydrous sugar alcohol, comprising a step of producing a sugar alcohol by the method according to claim 1, and a step of subjecting the sugar alcohol to a dehydration reaction.

5. The method according to claim 4, wherein the anhydrous sugar alcohol comprises a sorbitan and/or a xylitan as a main component.

6. A method of producing an anhydrous sugar alcohol ester, comprising a step of producing an anhydrous sugar alcohol by the method according to claim 4, and a step of subjecting the anhydrous sugar alcohol to a condensation reaction with a saturated or unsaturated fatty acid.

7. The method according to claim 6, wherein the anhydrous sugar alcohol ester comprises a sorbitan ester and/or a xylitan ester as a main component.

* * * * *